United States Patent [19]

Thamm et al.

[11] 4,260,422
[45] Apr. 7, 1981

[54] NOVEL PHOSPHONOCARBOXYLIC ACID COMPOUNDS

[75] Inventors: Horst-Dieter Thamm, Kelkheim; Volker Knittel, Wiesbaden; Werner Sommer; Gerhard Weckler, both of Sulzbach, all of Fed. Rep. of Germany

[73] Assignee: Hoechst Aktiengesellschaft, Frankfurt am Main, Fed. Rep. of Germany

[21] Appl. No.: 73,653

[22] Filed: Sep. 10, 1979

Related U.S. Application Data

[63] Continuation of Ser. No. 843,144, Oct. 17, 1977, abandoned.

[51] Int. Cl.³ ............................................. C04B 11/14
[52] U.S. Cl. ..................................... 106/111; 106/315
[58] Field of Search ........................ 106/111, 314, 315; 260/932

[56] References Cited

U.S. PATENT DOCUMENTS

| | | | |
|---|---|---|---|
| 3,941,772 | 3/1976 | Ploger et al. | 106/111 |
| 4,034,086 | 7/1977 | Ploger et al. | 106/111 |

*Primary Examiner*—James Poer
*Attorney, Agent, or Firm*—Curtis, Morris & Safford

[57] ABSTRACT

Novel phosphonocarboxylic acid compounds having the formula

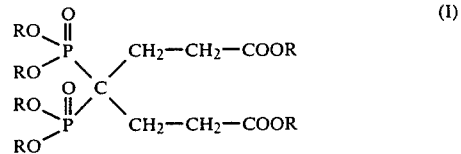

wherein the radicals R which may be identical or different and which represent alkyl radicals with 1–18 carbon atoms which may be optionally substituted by halogen, hydrogen, alkali metal ions or ammonium ions, are prepared by reacting methylene phosphonic acid alkyl esters with acrylic acid esters in the presence of strongly basic catalysts at temperatures of about 0°–140° C., and by possibly trans-esterifying the reaction products or by submitting the latter to acid or basic hydrolysis. The acid hydrolysis to yield the free 3,3-diphosphono-pimelic acid is best carried out with at least the about 6-fold molar quantity of a carboxylic acid such as HCOOH, CH₃COOH, etc., optionally in the presence of catalytic quantities of strong acids or bases, at elevated temperatures.

The compounds of formula (I), wherein the radicals R represent only alkyl radicals which may possibly be substituted by halogen, are valuable plasticizers for polyvinyl chloride, the compounds of formula (I), wherein R=H, alkali metal ions and/or ammonium ions, are valuable gypsum setting retardants and complex-forming agents for metal ions.

3 Claims, No Drawings

NOVEL PHOSPHONOCARBOXYLIC ACID COMPOUNDS

This is a continuation of application Ser. No. 843,144 filed Oct. 17, 1977, now abandoned.

The addition of methane diphosphonic acid tetraethyl ester to various olefinically unsaturated compounds in the presence of alkaline catalysts—especially of sodium ethylate—has been described by Russian authors (A. N. Pudovik, G. E. Yastrebova, Zh Obsch.-Khim. 40, 499, 1970). In the case of using e.g. acrylonitrile as olefinically unsaturated compound the product is said to be an adduct of 1 mol of methane diphosphonic acid tetraethyl ester and 2 mols of acrylonitrile; with the use of different olefinically unsaturated compounds such as vinyl phosphonic acid diethyl ester and acrylic acid methyl ester the result is said to have been only the mono-addition product i.e. the product of 1 mol of methane diphosphonic acid tetraethyl ester and 1 mol of the unsaturated compound. The final purpose of the thus obtained compounds is not explained in the Russian study.

With the intention to extend the obviously interesting reaction described by the Russian authors to cover also other syntheses and also to find useful applications for the compounds obtainable by such syntheses, it has been found now, that under the influence of alkaline catalysts it is generally possible to react 1 mol of methane diphosphonic acid tetraalkyl ester also with 2 mols of acrylic acid ester. The thus obtained di-adducts are novel derivatives of phosphonocarboxylic acids that represents, for example, excellent plasticizers for polyvinyl chloride. The pertinent free phosphonocarboxylic acids and the salts thereof, especially the alkali metal salts and the ammonium salts, are, for example, valuable gypsum setting retardants and complex forming agents for various metal ions.

Thus, the subject of the present invention is phosphonocarboxylic acid compounds having formula I

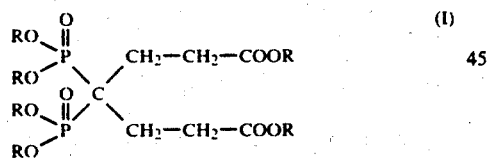

wherein the radicals R which may be identical or different and, have the following meaning:
alkyl radicals, preferably those with 1–18, especially 1–8 carbon atoms, which additionally may be substituted by halogen once to thrice (preferably by Cl and/or by Br),
hydrogen,
alkali metal ions (preferably Na ions and K ions) and NH$_4$ ions.

As alkyl radicals, optionally substituted by halogen, there may be cited for example:
CH$_3$, C$_2$H$_5$, n— and i—C$_3$H$_7$, C$_4$H$_9$, C$_5$H$_{11}$, C$_6$H$_{13}$, C$_7$H$_{15}$, C$_8$H$_{17}$, C$_{10}$H$_{21}$, C$_{14}$H$_{29}$, C$_{18}$H$_{37}$, cyclopentyl, cyclohexyl,
—CH$_2$—CH$_2$Cl, —(CH$_2$)$_3$Br, —(CH$_2$)$_2$—CHCl—CH$_3$ etc. Preferably these radicals are identical in pairs.

As compounds being covered by formula (I) there may be cited, for example:

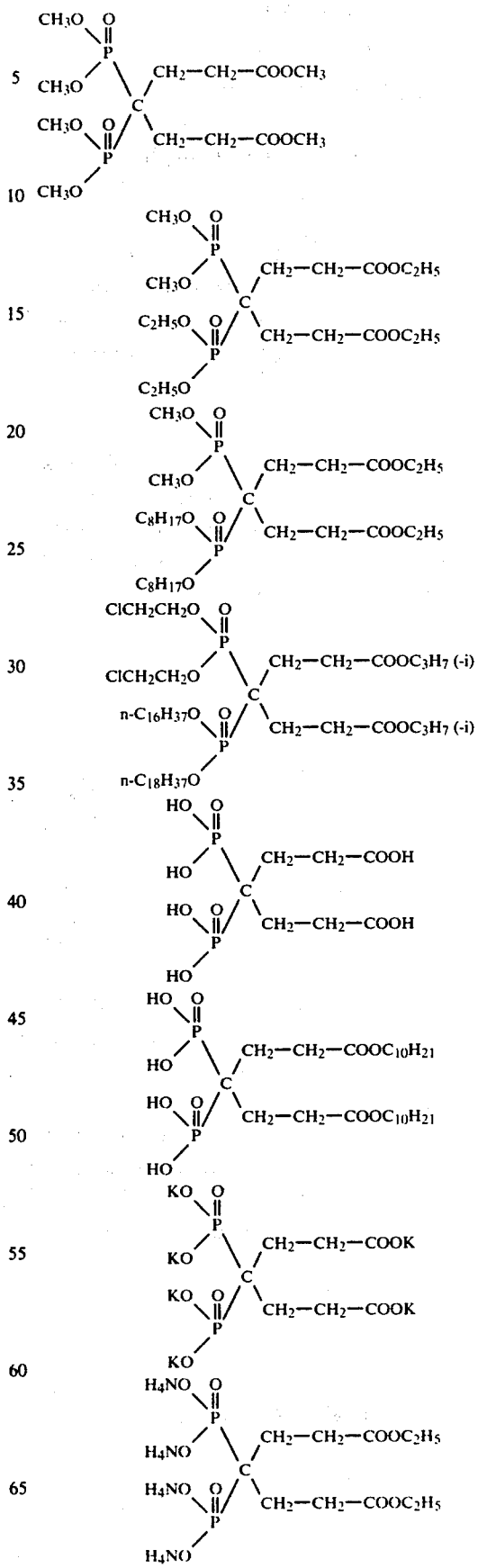

-continued

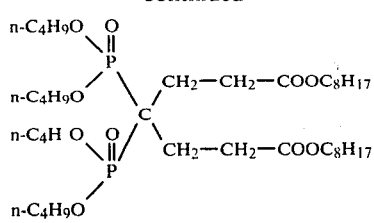

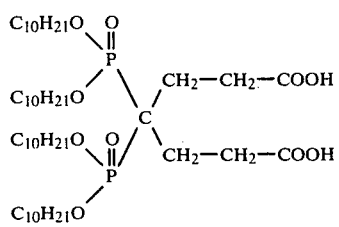
etc.

The novel compounds that are to be understood as derivatives of 3,3-diphosphono-pimelic acid, or —if R=H—represent 3,3-diphosphono-pimelic acid itself, are prepared by reacting methane diphosphonic acid tetraalkyl esters of formula (II)

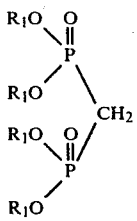 (II)

with acrylic acid esters of formula $$CH_2=CH-COOR_1 \quad (III)$$

wherein in both formulae (II) and (III) the radicals $R_1$, which may be identical or different, represent the same alkyl radicals—optionally substituted by halogen—as indicated for R in formula (I), at a molar ratio of about 1:2 in the presence of strongly basic catalysts at temperatures of about 0°–140° C., preferably of about 20°–100° C. and especially of about 40°–80° C.

The reaction is carried out according to the following reaction scheme:

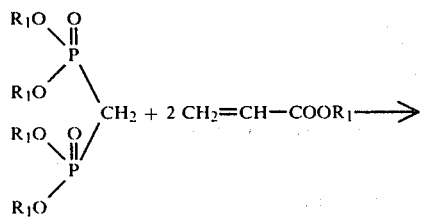

(II)    (III)

-continued

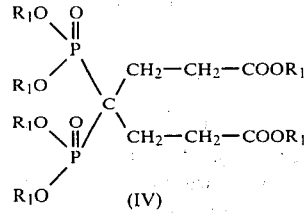
(IV)

Thus, there are first obtained the esters (IV) of 3,3-diphosphono-pimelic acid, i.e. those compounds of formula I, wherein R represents only the alkyl radicals, which may be optionally substituted by halogen, but does not represent either H or the alkali metal ions or ammonium ions. If so desired, the esters may be transesterified in known manner to yield different esters. The free acid and the alkali metal salts and ammonium salts are obtained from the esters (IV), also in known manner, by acid or alkaline hydrolysis. The acid hydrolysis of the esters (IV), wherein $R_1$ is an alkyl radical, optionally substituted by halogen, having only from 1–5, preferably from 1–2 carbon atoms, is carried out especially advantageously by heating with at least a six-fold molar quantity of a carboxylic acid, optionally in the presence of catalytic quantities of strong acids or bases.

The methane diphosphonic acid tetraalkyl esters of formula (II), that are used as starting substances of the reaction, may be prepared according to various processes known in the specialized literature, for example (a) by reaction of trialkyl phosphites with halogen methane phosphonic acid dialkyl esters with the isolation of the pertinent alkyl halides (J. A. Cade, J.Chem.-Soc. 1959, 2266), or (b) by reaction of alkali dialkyl phosphites and halogen methane phosphonic acid dialkyl esters with the elimination of alkali halides (G. Schwarzenbach, Y. Zurc, Monatsh. 81, 202, 1950).

The following examples may be cited to illustrate methane diphosphonic acid tetraalkyl esters of formula II: methane diphosphonic acid tetramethyl ester, -tetraethyl ester, -tetra-2-chloroethyl ester, -tetra-isopropyl ester, -tetra-butyl ester, -tetra-hexyl ester, -tetra-decyl ester, -tetra-dodecyl ester, -tetra-octadecyl ester, -dimethyl diethyl ester, -dimethyl dipropyl ester, -dimethyl-di-tert.-butyl ester, -diethyl-dihexyl ester, -diethyl dioctyl ester, -di-2-chloroethyl didecyl ester.

The acrylic acid esters of formula III to be used for carrying out the reaction are known and are prepared to a large extent on an industrial scale. There may be mentioned the following examples thereof: acrylic acid methyl ester, -ethyl ester, -isopropyl ester, -tert.-butyl ester, -hexylester, -2-ethylhexyl ester, -dodecyl ester, -octadecyl ester, -cyclohexyl ester.

There are used as reaction catalysts: strong bases such as alcoholates, hydrides, quart. ammonium hydroxides (which may be used as strongly basic ion exchangers), etc. Preference is given to the use of alkali alcoholates, as well as alkalihydrides and -amides. Especially preferred are the sodium compounds and potassium compounds.

The reaction according to the invention can be carried out in the presence as well as in absence of a solvent or diluent; suitable solvents are all organic solvents that are inert under the reaction conditions such as aliphatic and aromatic hydrocarbons, ethers and alcohols, e.g. n-pentane, n-hexane, decane, toluene, xylene, tetrahydrofurane, diethyl ether, diisopropylether, dioxane, methanol, ethanol, isopropanol.

The reaction temperatures may vary within a wide range. The reaction generally takes place at temperatures from about 0° to 140° C., preferably from about 20° to 100° C., especially at from 40° to 80° C. Since the additive reaction exhibits an exothermic behavior, a cooling step may be needed.

The process according to the present invention is carried out with the reactants II and III being blended preferably at the ratio of about 1:2, an excess of component III up to about 10% being possible. Subsequently the basic catalyst (e.g. sodium methylate in alcoholic solution)-generally from about 0.01 to 0.25 mol, preferably from about 0.03 to 0.15, especially from about 0.04 to 0.08 mol of basic catalyst per mol of methane diphosphonic acid tetraalkyl ester—is added slowly. The reaction temperature and the rate may be regulated either by cooling from the outside or by control of the rate of addition of the catalyst.

The adducts IV are formed at a sufficient degree of purity according to the process of the invention, so that they may be used directly for further work-up, after in vacuo distillation of the volatile components.

The catalyst portions, especially those of long-chain phosphonocarboxylic acid esters, are removed most conveniently by a treatment with water and charcoal and the removal is necessary for the use of the adducts as plasticizers for PVC.

The acid by hydrolysis of the adducts of formula IV is carried out quantitatively according to known processes, such as by the action of anhydrous hydrogen chloride at temperatures of from about 130° to 160° C., optionally under pressure, by boiling over a prolonged period of time at about 70° to 110° C., or by reaction with at least the stoichiometrically necessary quantity of water in the presence of phosphonocarboxylic acid of formula I (R=H) at temperatures of from about 160° to 250° C., while distilling off the newly formed volatile components.

If the acidolytic treatment is carried out according to one of these processes, the phosphonocarboxylic acid is then obtained according to the invention, perhaps dissolved in hydrochloric acid or water, and may be isolated in its anhydrous state by distilling off water and/or hydrochloric acid in vacuo and at temperatures of up to about 150° C.

Especially good results are obtained with the acidolytic treatment of esters of formula (IV), wherein $R_1$ represents an alkyl radical, possibly substituted by halogen, with 1-5, preferably 1 to 2 carbon atoms, in analogy to the process known from German Offenlegungsschrift No. 2,518,144 (acidolysis of carboxy alkane phosphonic acid alkyl esters and of carboxy alkylphosphonic acid alkyl esters with at least 1 mol of formic acid per ester group at about 80°-140° C.), carried out by heating with at least a 6-fold molar quantity of a carboxylic acid having formula $$R_2COOH \qquad (V)$$

wherein $R_2$ means hydrogen,
an alkyl group having 1 to 8 carbon atoms, optionally substituted by 1-3 halogen atoms, especially chlorine atoms,
a $(C_2-C_4)$-alkylene radical,
a $(C_5-C_6)$-cycloalkyl radical or a phenyl radical, possibly in the presence of catalytic quantities of strong acids or bases at temperatures of about 100° to 200° C., preferably at about 120° to 160° C.: the thus formed carboxylic acid alkyl esters are then distilled off and the 3,3-diphosphonopimelic acid is isolated in known manner.

Carboxylic acids of formula V suitable for acidolytic treatment are for example: formic acid, acetic acid, chloroacetic acid, propionic acid, caproic acid, acrylic acid, benzoic acid, etc., especially formic acid, acetic acid and propionic acid. Mixtures of these acids may be used as well, of course.

The carboxylic acids of formula V are used at least in stoichiometric quantities, i.e. 1 mol of ester group per mol of starting ester, that means, the use of at least an approximately 6-fold molar quantity of carboxylic acid of formula V, since the starting ester contains 6 ester groups. Generally, the carboxylic acid of formula V is used at an excess of about 10-200%, preferably from about 20-100%. Larger quantities are possible, but as a rule they do not bring about any advantage. The excess of carboxylic acid may be removed by distillation after terminating the reaction. The carboxylic acids of formula V may be used in an industrial quality grade.

The acidolytic operation may be carried out in a simple manner by heating the mixture of the components and by distilling off the carboxylic acid alkyl ester. It is preferable to charge beforehand one component, especially the starting ester, with part of the other reactant and optionally with a catalyst, and to add the reset after the reaction temperature has been reached, while meanwhile distilling off the carboxylic acid esters formed. As soon as the reaction has terminated, the excess carboxylic acid is also distilled off, or cooling takes place followed by separating by suction filtration the precipitated acid of formula I (i.e. R=H; 3,3-diphosphonopimelic acid). In case of a minor excess of carboxylic acid of formula V, dilution with water may also take place in order to obtain a mixture suitable for agitation. When reacting the starting ester and the carboxylic acid of formula V there are formed on one hand the free 3,3-diphosphonopimelic acid, on the other hand the corresponding alkyl esters of carboxylic acid of formula V, that are distilled off proportionately to their formation, this removal being eventually carried out under a reduced pressure which depends on the boiling point of the newly formed ester. The removal by distillation is most usefully carried out by means of a fractionating column, in order to prevent larger quantities of carboxylic acid of formula V from being removed in the distillation. In that case the carboxylic acid alkyl esters may be obtained in a good purity which permits them to be worked up directly, for example as solvents or as starting materials for organic syntheses.

The most expedient way of carrying out the acidolytic operation is by catalysis in the presence of strong acids or bases.

As examples of suitable catalysts there may be cited: sulfuric acid, phosphoric acid, p-toluene-sulfonic acid, the very phosphonocarboxylic acid formed during the reaction, acid ion exchange resins, NaOH, KOH. When using bases, these occur as salts of the carboxylic acids of formula V.

It is preferable to use acid catalysts, especially of p-toluene-sulfonic acid and sulfuric acid. Generally, there are added to the reaction mixture about 0.01-0.25 mol, preferably 0.02-0.05 mol of the pertinent catalyst per mol of the starting ester. Larger quantities are possible, especially in case that the 3,3-diphosphonopimelic acid itself is employed as catalyst.

The aqueous-alkali hydrolysis of ester of formula (IV) leads in known manner to salts of formula (I) (R=alkali metal ions or ammonium ions), a gradual or partial hydrolysis being also possible, of course. The compounds covered by formula (I) may be converted from one to another by means of known operations. They are valuable products serving many purposes and being applicable directly.

Esters of formula (I) for example, i.e. those compounds covered by formula (I), the radicals R of which are only alkyl radicals, optionally substituted by halogen, and at least 2 radicals of which have from 4–10, preferably from 6–8 carbon atoms, make excellent plasticizers for polyvinyl chloride. For this purpose especially preferred esters of formula (I) are those, the phosphonic ester groups of which contain an alkyl radicals R methyl groups or ethyl groups and the carboxylic acid ester groups of which contain as alkyl radicals R hexyl, heptyl or octyl radicals. They impart additionally to the thus formulated compositions excellent flame-retarding or auto-extinguishing properties.

When using these phosphonocarboxylic acid esters as plasticizers for polyvinyl chloride, the most favorable ratio thereof varies from 20 to 50 weight %, preferably from about 30 to 40 weight %, calculated on the total composition; that means phr values (parts of plasticizer per hundred parts of resin) advantageously ranging from 25 to 100, especially from 42 to 67.

The phosphonocarboxylic acid esters may be added to the aqueous polyvinyl chloride dispersion; preference is given, however, to the addition to the polymer composition.

The free phosphonocarboxylic acid (R=H) covered by formula (I) and the acidic alkali metal salts and/or ammonium salts are valuable retarding agents for the setting of gypsum and are superior to the citric acid industrially used for that purpose. There are added to the gypsum paste most advantageously about 0.06–0.09, preferably 0.07 to 0.08 weight % of the novel compounds.

The free phosphonocarboxylic acid and its alkali metal and/or ammonium salts (which react as alkali) and also the acid salts containing furthermore one or several free acid groups, are valuable complex forming agents for metal ions, especially for heavy metal ions such as the ions of iron, but also for alkaline earth metal ions. Thus, the novel complex forming agents prevent precipitation from water of e.g. alkaline earth metals and of iron (present as hydroxides) or of carbonates. Therefore, they are suitable for water softening. There is no need to use stoichiometric quantities, hence it is possible to prevent precipitation of calcium salt by using quantities below the stoichiometric level.

The novel properties have the effect that the novel complex-forming agents may be used e.g. for cleaning glass articles, especially appropriate is their use as additive for rinsing bottles.

The following examples illustrate the invention:

EXAMPLES OF PREPARATION

Example 1

3,3-diphosphonopimelic acid

A reaction flask equipped with agitator, reflux cooler, thermometer and dropping funnel, is charged with 400 g (4.0 mols) of acrylic acid ethyl ester and 564 g (2.0 mols) of methane diphosphonic acid tetraethyl ester, at room temperature, while stirring. Within 60 minutes there are added dropwise to this mixture 40 g of a 33%-strength methanolic sodium methylate solution, while maintaining the interior temperature at maximum 70° C. by means of an external cooler. The reaction is allowed to continue for another 3 hours' period, the thus obtained 3,3-diphosphonopimelic acid hexaethyl ester is then freed from volatile components by distillation in vacuo up to a kettle temperature of 110° C. The degree of purity of the thus obtained product is examined by thin-layer chromatography and proves to be above 95%.

Crude yield: 980 g (99% of the theoretical yield).

$C_{19}H_{38}O_{10}P_2$ (MG 488). Analysis: Calc.: C 46.72%; H, 7.78%; P 12.70%. Found: C 46.3%; H 7.8%; P 12.5%.

The thus obtained ester is heated to the boiling temperature (which rises from 90° to about 112° C.) with 2500 ml of concentrated hydrochloric acid for 12 hours, while ethyl chloride and ethanol formed during the acidolytic treatment are distilled off.

The reaction solution is evaporated to dryness in vacuo at the end of the reaction (maximum sump temperature 120° C.). The remaining solid residue is dried at 100° C. in vacuo, yielding 590 g of 3,3-diphosphonopimelic acid (92% of the theoretical yield), having a fusion point of 250°–252° C. (with decomposition).

$C_7H_{14}O_{10}P_2$ (MG 320). Analysis: Calc.: C 26.25%; H 4.37%; P 19.37%. Found: C 25.8%; H 4.5%; P 19.2%.

Acidolytic treatment of 3,3-diphosphonopimelic acid-hexaethyl ester
(=3,3-diphosphonotetraethyl-pimelic acid diethyl ester) with carboxylic acids:

(a) 244 g (0.5 mol) of 3,3-diphosphonotetraethyl-pimelic acid diethyl ester are introduced into a reaction flask with agitator, thermometer, dropping funnel and distillation device with packed column, and blended with 2.5 g (0.025 mol) of concentrated sulfuric acid. Of a total quantity of 276 g (6.0 mol) of formic acid there are first added 70 g (approximately 25%), and the mixture is then heated to 135°–140° C. The thus formed formic acid ethyl ester is distilled off constantly, while the remaining formic acid is added slowly dropwise over a 6 hours' period. At the end of the reaction the excess of formic acid is also removed by distillation in vacuo.

Yield: 148 g (89.6% of the theoretical yield); fusion point 246°–248° C. (with decomposition).

(b) According to the processing method (a) there are reacted 244 g (0.5 mol) of 3,3-diphosphonotetraethyl pimelic acid diethyl ester after having added at 135°–140° C. 8.3 g (0.025 mol) of 3,3-diphosphonopimelic acid, with 276 g (6.0 mol) of formic acid. The reaction time is 10 hours. After work-up according to Example (1) the product is a free acid.

Yield: 150 g (85.8% of the theoretical yield); fusion point 246°–248° C. (with decomposition).

(c) According to the processing method (a) there are reacted at 135°–140° C. 244 g (0.5 mol) of 3,3-diphosphonotetraethyl-pimelic acid diethyl ester with 360 g (6.0 mol) of acetic acid after having added 2.5 g (0.025 mol) of concentrated sulfuric acid. The reaction time is 8 hours. The thus formed acid crystallizes in course of the reaction. Acetic acid also present is subsequently removed by distillation in vacuo.

Yield: 152 g (95% of the theoretical yield), fusion point: 248°–250° C. (with decomposition).

(d) According to processing method (a) there are reacted at 140° C. 244 g (0.5 mol) of 3,3-diphosphonotetraethyl-pimelic acid diethyl ester with 360 g (6.0 mol) of acetic acid, after having added 4.3 g (0.025 mol) of p-toluene sulfonic acid. The reaction time is about 10 hours. After cooling, the precipitated acid is suction filtered.

Yield: 152 g (92% of the theoretical yield); fusion point: 248°–249° C. (with decomposition).

(e) According to the processing method (a) there are reacted at 145°–150° C. over a period of about 10 hours 122 g (0.25 mol) of 3,3-diphosphonotetraethyl-pimelic acid diethyl ester with 222 g (3.0 mol) of propionic acid, after having added 1.5 g (0.015 mol) of concentrated sulfuric acid. The crystal acid is suction filtered after cooling.

Yield: 70 g (84.8% of the theoretical yield); fusion point: 246°–248° C. (with decomposition).

(f) 122 g (0.25 mol) of 3,3-diphosphonotetraethyl-pimelic acid diethyl ester are reacted at 140°–145° C. according to the processing method (a) with 138 g (3.0 mol) of formic acid. The reaction time is about 12 hours. At the end of the reaction the excess of formic acid is removed in vacuo.

Yield: 68 g (85% of the theoretical yield), fusion point: 246°–247° C.

Example 2

3,3-Diphosphonotetraethyl-pimelic acid-di-n-octyl ester 10 g of methanolic sodium methylate solution of 33% strength are added dropwise within 30 minutes to a mixture of 72 g (0.25 mol) of methane diphosphonic acid tetraethyl ester and 92 g (0.5 mol) of acrylic acid-n-octyl ester. During this operation the internal temperature rises to about 80° C. At this temperature the reaction is allowed to continue for another hour and, after cooling, the mixture is then blended with about 100 ml of water and some charcoal. After stirring for 30 minutes, filtration takes place, the aqueous phase is separated and the organic phase is freed from volatile components by distillation in vacuo up to a sump temperature of 110° C. There are obtained 154 g of 3,3-diphosphonotetraethyl-pimelic acid-di-n-octyl ester (94% of the theoretical yield).

$C_{31}H_{62}O_{10}P_2$ (MG 656). Analysis: Calc.: C 56.7%; H 9.45%; P 9.45% Found: C 56.1%; H 9.3%; P 9.5%

EXAMPLES OF APPLICATION

Example I

Gypsum setting retardant

Test method: Method Vicat according to DIN 1168
Water equivalent of gypsum: 0.60

| Test product | quantity added (wgt. %) | Setting time of the stucco gypsum start | end |
|---|---|---|---|
| 3,3-diphosphono-pimelic acid (accdg. to invention) | 0.075 | abt. 185 min. | 200 min. |
|  | 0.10 | >390 min. | — |
| citric acid (comparison) | 0.075 | 140 min. | 155 min. |
|  | 0.10 | 170 min. | 187 min. |

Example II

Plasticizer for polyvinyl chloride (PVC)

From a mixture consisting of
100 parts by weight of suspension PVC, K value 70,
70 parts by weight of 3,3-diphosphonotetraethyl-pimelic acid-di-n-octyl ester (according to invention)
3 parts by weight of epoxidized soja oil (epoxide oxygen 6.5%)
2 parts by weight of barium-cadmium-laureate,
0.3 part by weight of glycerin monostearate and
0.1 part by weight of stearic acid
was prepared a dry-blend and therefrom a 0.5 mm thick PVC soft sheet was prepared by extrusion. The above specified mixture exhibits excellent gelating properties at temperatures of 150° C.

The resulting sheet is limpid as water, without any specks and the surface being non-adhesive. The sheet is very solid, hardly igniting, and auto-extinguishing. A special feature is also the good flexibility of the sheet at temperatures from below 0° C. to −50° C.

Example III

Complex-forming agent for metal ions

The complex forming properties of phosphonocarboxylic acid according to the invention were determined as reference for measuring the calcium binding ability according to known methods. The calcium binding ability indicates, how many milligrams of calcium ions are maintained in solution per gram of complex-forming agent.

The following table states the calcium binding ability of some commercially available complex-forming agents, compared with the phosphonocarboxylic acid of the invention.

TABLE

| Complex forming agent | Calcium binding ability mg $Ca^{3+}$/g complex forming agent |
|---|---|
| pentasodiumtriphosphate (known) (pH 10) | 95 |
| trisodiumnitrilotriacetic acid (known) (pH 10) | 148 |
| 1-hydroxyethane-1,1-diphosphonic acid (known) (pH 10–12) | 240 |
| 1,3-dicarboxy-3-methylpropane-1-phosphonic acid (known) (pH 10) | 273 |
| 3,3-diphosphonopimelic acid (pH 11–12) (according to the invention) | 412 |

What is claimed is:

1. The method of retarding the setting of gypsum paste which comprises incorporating in gypsum paste from 0.06% to 0.09% by weight of a phosphonocarboxylic compound of the formula

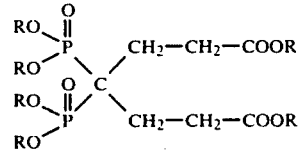

wherein the radicals R are selected from hydrogen, alkali metal and ammonium.

2. A method according to claim 1 wherein R is alkali metal selected from sodium and potassium.

3. A method according to claim 1 wherein the phosphonocarboxylic compound is 3,3-diphosphono-pimelic acid.

* * * * *

UNITED STATES PATENT AND TRADEMARK OFFICE
CERTIFICATE OF CORRECTION

PATENT NO. : 4,260,422
DATED : April 7, 1981
INVENTOR(S) : Thamm et al.

It is certified that error appears in the above—identified patent and that said Letters Patent are hereby corrected as shown below:

On the title page, under Item [63], insert:

[30]  October 19, 1976    Germany  ......... 26 47 042.8

April 30, 1977     Germany  ......... 27 19 415.6

Signed and Sealed this

Twenty-seventh Day of July 1982

[SEAL]

Attest:

GERALD J. MOSSINGHOFF

Attesting Officer      Commissioner of Patents and Trademarks